United States Patent [19]

Bird et al.

[11] Patent Number: 5,126,365
[45] Date of Patent: Jun. 30, 1992

[54] BICYCLIC DERIVATIVES

[75] Inventors: Thomas G. C. Bird, Witry-Les-Reims, France; John F. Kingston; David Waterson, both of Macclesfield, England

[73] Assignees: Imperial Chemical Industries PLC, London, England; ICI Pharma, Cergy, France

[21] Appl. No.: 557,103

[22] Filed: Jul. 25, 1990

[30] Foreign Application Priority Data

Jul. 26, 1989 [EP] European Pat. Off. ......... 894021278

[51] Int. Cl.$^5$ ..................... A61K 31/35; C07D 407/00
[52] U.S. Cl. .................... 514/451; 514/459; 514/460; 549/414
[58] Field of Search ................ 536/18.1; 549/414; 514/451, 459, 460

[56] References Cited

U.S. PATENT DOCUMENTS

| | | | |
|---|---|---|---|
| 2,434,856 | 1/1948 | La Forge | 549/414 |
| 3,661,917 | 5/1972 | Kaiser et al. | 546/232 |
| 3,743,737 | 7/1973 | Kaiser et al. | 514/331 |
| 3,795,740 | 3/1974 | Baker | 549/414 X |
| 3,917,597 | 11/1975 | Regnier et al. | 514/314 |
| 4,010,267 | 3/1977 | Regnier et al. | 514/314 |
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/307 |
| 4,725,619 | 2/1916 | Chakraborty et al. | 514/442 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 514/314 |
| 4,876,346 | 10/1989 | Musser et al. | 546/172 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |

FOREIGN PATENT DOCUMENTS

| | | |
|---|---|---|
| 0110405 | 6/1984 | European Pat. Off. |
| 0181568 | 5/1986 | European Pat. Off. |
| 0190722 | 8/1986 | European Pat. Off. |
| 0200101 | 12/1986 | European Pat. Off. |
| 0271287 | 6/1988 | European Pat. Off. |
| 0349062 | 6/1989 | European Pat. Off. |

OTHER PUBLICATIONS

Taylor et al., The Leukotriene Biosynthetic Pathway: A Target for Pharmacological Attack, TIPS, Mar. 1986.
Aharony et al., Kinetic Mechanism of Guinea Pig Neutrophil 5-Lipoxygenase, The Journal of Biological Chemistry, vol. 261, No. 25, pp. 11512-11519, Sep. 5, 1986.
Carey et al., Development and Characterization of a Radioimmunoassay for Leukotriene B$_4$, 34P, 1986.
Humes et al., Pharmacological Effects of Non-Steroidal Antiinflammatory Agents on Prostaglandin and Leukotriene Synthesis in Mouse Peritoneal Macrophages, Biochemical Pharmacology, vol. 32, No. 15, pp. 2319-2322, 1983.
Aked et al., The Inflammatory Response of Rabbit Skin to Topical Arachidonic Acid and Its Pharmacological Modulation, Br. J. Pharmac. (1986) 89, 431-338.
Anderson et al., An In Vivo Model for Measuring Antigen-Induced SRS-A-Mediated Bronchoconstriction and Plasma SRS-A Levels in the Guinea-Pig, Br. J. Pharmac. (1983) 78, 067-074.

*Primary Examiner*—C. Warren Ivy
*Assistant Examiner*—Catherine Scalzo
*Attorney, Agent, or Firm*—Cushman, Darby & Cushman

[57] ABSTRACT

The invention concerns a bicyclic derivative of the formula I, or a pharmaceutically-acceptable salt thereof,

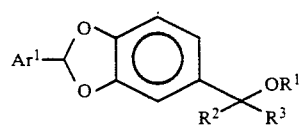

wherein Ar$^1$ is optionally substituted phenyl or naphthyl;
R$^1$ if (1-6C)alkyl, (3-6C)alkenyl, (3-6C)alkynyl, cyano-(1-4C)alkyl or (2-4C)alkanoyl, or optionally substituted benzoyl; and
R$^2$ and R$^3$ together form a group of the formula —A$^1$—X—A$^2$—, wherein each of A$^1$ and A$^2$ is (1-4C)alkylene and X is oxy, thio, sulphinyl, sulphonyl or imino.

The invention also concerns processes for the manufacture of a bicyclic derivative of the formula I, or a pharmaceutically-acceptable salt thereof, and pharmaceutical compositions containing said bicyclic derivatives. The compounds of the invention are inhibitors of the enzyme 5-lipoxygenase.

8 Claims, No Drawings

BICYCLIC DERIVATIVES

This invention concerns novel bicyclic derivatives and more particularly novel bicyclic derivatives which are inhibitors of the enzyme 5-lipoxygenase (hereinafter referred to as 5-LO). The invention also concerns processes for the manufacture of said derivatives and novel pharmaceutical compositions containing them. Also incuded in the invention is the use of said derivatives in the treatment of various inflammatory and/or allergic diseases in which the direct or indirect products of 5-LO catalysed oxidation of arachidonic acid are involved, and the production of new medicaments for such use.

As stated above the bicyclic derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100-103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain bicyclic derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a bicyclic derivative of the formula I (set out hereinafter) wherein $Ar^1$ is phenyl or naphthyl which may optionally bear one or more substituents selected from amino, halogeno, hydroxy, cyano, (1–4C)alkyl, (2–4C)alkenyl, (2–4C)alkynyl, (1–4C)alkoxy, (1–4C)alkylthio, (1–4C)alkylsulphinyl, (1–4C)alkylsulphonyl, (1–4C)alkylamino, di-[(1–4C)alkyl]amino, (1–4C)alkoxycarbonyl, (2–4C)alkanoyl, hydroxy-(1–4C)alkyl, fluoro-(1–4C)alkyl, cyano-(1–4C)alkyl, fluoro-(1–4C)alkoxy, cyano-(1–4C)alkoxy, phenyl and benzoyl, and wherein said phenyl or benzoyl substituent may optionally bear a substituent selected from halogeno, (1–4C)alkyl and (1–4C)alkoxy;

wherein the bicyclic ring may optionally bear one or two substituents selected from halogeno, hydroxy, (1–4C)alkyl, (1–4C)alkoxy and fluoro-(1–4C)alkyl;

wherein $R^1$ is (1–6C)alkyl, (3–6C)alkenyl, (3–6C)alkynyl, cyano-(1–4C)alkyl or (2–4C)alkanoyl or $R^1$ is benzoyl which may optionally bear a substituent selected from halogeno, (1–4C)alkyl and (1–4C)alkoxy; and wherein $R^2$ and $R^3$ together form a group of the formula $-A^1-X-A^2-$ which, together with the carbon atom to which $A^1$ and $A^2$ are attached, defines a ring having 4 to 7 ring atoms, wherein $A^1$ and $A^2$, which may be the same or different, each is (1–4C)alkylene and X is oxy, thio, sulphinyl, sulphonyl or imino, and which ring may bear one or two substituents, which may be the same or different, selected from halogeno, hydroxy, (1–4C)alkyl, (1–4C)alkoxy, (1–4C)alkylthio, (1–4C)alkylsulphinyl and (1–4C)alkylsulphonyl or which ring may bear a (1–4C)alkylenedioxy substituent;

or a pharmaceutically-acceptable salt thereof.

According to a further feature the invention there is provided a bicyclic derivative of the formula I wherein $Ar^1$ is phenyl or naphthyl which may optionally bear one or more substituents selected from amino, halogeno, hydroxy, cyano, (1–4C)alkyl, (2–4C)alkenyl, (2–4C)alkynyl, (1–4C)alkoxy, (1–4C)alkylthio, (1–4C)alkylsulphinyl, (1–4C)alkylsulphonyl, (1–4C)alkylamino, di-[(1–4C)alkyl]amino, (1–4C)alkoxycarbonyl, (2–4C)alkanoyl, hydroxy-(1–4C)alkyl, fluoro-(1–4C)alkyl, cyano-(1–4C)alkyl, fluoro-(1–4C)alkoxy and cyano-(1–4C)alkoxy;

wherein the bicyclic ring may optionally bear one or two substituents selected from halogeno, hydroxy, (1–4C)alkyl, (1–4C)alkoxy and fluoro-(1–4C)alkyl;

wherein $R^1$ is (1–6C)alkyl, (3–6C)alkenyl, (3–6C)alkynyl, cyano-(1–4C)alkyl or (2–4C)alkanoyl or $R^1$ is benzoyl which may optionally bear a substituent selected from halogeno, (1–4C)alkyl and (1–4C)alkoxy; and wherein $R^2$ and $R^3$ together form a group of the formula $-A^1-X-A^2-$ which, together with the carbon atom to which $A^1$ and $A^2$ are attached, defines a ring having 4 to 7 ring atoms, wherein $A^1$ and $A^2$, which may be the same or different, each is (1–4C)alkylene and X is oxy, thio, sulphinyl, sulphonyl or imino, and which ring may bear one or two substituents, which may be the same or different, selected from halogeno, hydroxy, (1–4C)alkyl, (1–4C)alkoxy, (1–4C)alkylthio, (1–4C)alkylsulphinyl and (1–4C)alkylsulphonyl or which ring may bear a (1–4C)alkylenedioxy substituent;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more asymmetric carbon atoms, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for a halogeno substituent which may be present on $Ar^1$, the bicyclic ring, $R^1$ or on a phenyl or benzoyl substituent on $Ar^1$, is, for example, fluoro, chloro, bromo or iodo.

A suitable value for a (1–4C)alkyl substituent which may be present on $Ar^1$, the bicyclic ring, $R^1$ or on a phenyl or benzoyl substituent on $Ar^1$, is, for example, methyl, ethyl, propyl, isopropyl, butyl, isobutyl, sec-butyl or tert-butyl.

A suitable value for a (2–4C)alkenyl substituent on $Ar^1$ is, for example, vinyl, allyl, 2-butenyl or 3-butenyl.

A suitable value for a (2–4C)alkynyl substituent on $Ar^1$ is, for example, ethynyl, 1-propynyl, 2-propynyl, 1-butynyl or 2-butynyl.

A suitable value for a (1–4C)alkoxy substituent which may be present on $Ar^1$, the bicyclic ring, $R^1$ or on a phenyl or benzoyl substituent on $Ar^1$ is, for example, methoxy, ethoxy, propoxy, isopropoxy or butoxy.

Suitable values for substituents which may be present on $Ar^1$ include, for example:
for (1–4C)alkylthio: methylthio, ethylthio, propylthio, isopropylthio and butylthio;
for (1–4C)alkylsulphinyl: methylsulphinyl, ethylsulphinyl, propylsulphinyl, isopropylsulphinyl and butylsulphinyl;
for (1–4C)alkylsulphonyl: methylsulphonyl, ethylsulphonyl, propylsulphonyl, isopropylsulphonyl and butylsulphonyl;
for (1–4C)alkylamino: methylamino, ethylamino, propylamino and butylamino;
for di-[(1–4C)alkyl]amino: dimethylamino, diethylamino and dipropylamino;
for (1–4C)alkoxycarbonyl: methoxycarbonyl, ethoxycarbonyl and tert-butoxycarbonyl;
for hydroxy-(1–4C)alkyl: hydroxymethyl, 1-hydroxyethyl, 2-hydroxyethyl, 1-hydroxypropyl, 2-hydroxypropyl and 3-hydroxypropyl;
for cyano-(1–4C)alkyl: cyanomethyl, 1-cyanoethyl, 2-cyanoethyl, 3-cyanopropyl and 2-cyanoprop-2-yl;
for cyano-(1–4C)alkoxy: cyanomethoxy, 2-cyanoethoxy and 3-cyanopropoxy;
for fluoro-(1–4C)alkoxy: trifluoromethoxy, 2,2,2-trifluoroethoxy and pentafluoroethoxy.

A suitable value for a fluoro-(1–4C)alkyl substituent which may be present on $Ar^1$ or on the bicyclic ring is, for example, fluoromethyl, difluoromethyl, trifluoromethyl, 2-fluoroethyl, 2,2,2-trifluoroethyl and pentafluoroethyl.

A suitable value for the number of substituents which may be present on $Ar^1$ is, for example, one, two or three.

A suitable value for a (2–4C)alkanoyl substituent which may be present on $Ar^1$ or for $R^1$ when it is (2–4C)alkanoyl is, for example, acetyl, propionyl, butyryl or isobutyryl.

A suitable value for $R^1$ when it is (1–6C)alkyl is, for example, methyl, ethyl, propyl, butyl, pentyl or hexyl; when it is (3–6C)alkenyl is, for example, allyl, 2-butenyl or 3-butenyl; and when it is (3–6C)alkynyl is, for example, 2-propynyl or 2-butynyl.

A suitable value for $R^1$ when it is cyano-(1–4C)alkyl is, for example, cyanomethyl, 2-cyanoethyl or 3-cyanopropyl.

When $R^2$ and $R^3$ together form a group of the formula $-A^1-X-A^2-$ which, together with the carbon atom to which $A^1$ and $A^2$ are attached, defines a ring having 4 to 7 ring atoms then a suitable value for $A^1$ or $A^2$, which may be the same or different, when each is (1–4C)alkylene is, for example, methylene, ethylene, trimethylene or tetramethylene.

Suitable values for the one or two substituents which may be present on said 4- to 7-membered ring include for example:
for halogeno: fluoro, chloro and bromo;
for (1–4C)alkyl: methyl, ethyl, propyl, isopropyl and butyl;
for (1–4C)alkoxy: methoxy, ethoxy, propoxy, isopropoxy and butoxy;
for (1–4C)alkylthio: methylthio, ethylthio, propylthio, isopropylthio and butylthio;
for (1–4C)alkylsulphinyl: methylsulphinyl, ethylsulphinyl, propylsulphinyl, isopropylsulphinyl and butylsulphinyl;
for (1–4C)alkylsulphonyl: methylsulphonyl, ethylsulphonyl, propylsulphonyl, isopropyl-sulphonyl and butylsulphonyl;
for fluoro-(1–4C)alkyl: fluoromethyl, difluoromethyl, trifluoromethyl, 2-fluoroethyl, 2,2,2-trifluoroethyl and pentafluoroethyl;
for (1–4C)alkylenedioxy: methylenedioxy and ethylenedioxy.

A suitable pharmaceutically-acceptable salt of a bicyclic derivative of the invention is, for example, an acid-addition salt of a bicyclic derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a bicyclic derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, bicyclic derivatives of the formula I wherein:
(a) $Ar^1$ is phenyl, naphth-1-yl or naphth-2-yl which may optionally bear one, two or three substituents selected from amino, fluoro, chloro, bromo, cyano, methyl, ethyl, propyl, isopropyl, tert-butyl, methoxy, methylthio, methylsulphinyl, methylsulphonyl, methoxycarbonyl, difluoromethyl, trifluoromethyl, 1-cyanoethyl, 2-cyanoethyl, 2-cyanoprop-2-yl and cyanomethoxy; and the bicyclic ring, $R^1$, $R^2$ and $R^3$ have any of the meanings defined hereinbefore;
(b) $Ar^1$ is phenyl or naphth-2-yl which may optionally bear one or two substituents selected from fluoro, chloro, cyano, methyl, ethyl, propyl, tert-butyl, methoxy, methylthio, methylsulphinyl, methylsulphonyl and 2-cyanoprop-2-yl; and the bicyclic ring $R^1$, $R^2$ and $R^3$ have any of the meanings defined hereinbefore;
(c) $Ar^1$ is phenyl which may optionally bear one or two substituents selected from fluoro, chloro, methyl, ethyl, propyl, tert-butyl, methylthio, methylsulphinyl, methylsulphonyl, trifluoromethyl, phenyl and benzoyl, and wherein said phenyl and benzoyl substituents may optionally bear a substituent selected from fluoro, chloro, methyl and methoxy; and the bicyclic ring, $R^1$, $R^2$ and $R^3$ have any of the meanings defined hereinbefore;

(d) The bicyclic ring may optionally bear one substituent selected from fluoro, chloro, hydroxy, methyl, methoxy and trifluoromethyl; and $R^1$, $R^2$ and $R^3$ have any of the meanings defined hereinbefore;

(e) $R^1$ is methyl, ethyl, allyl, 2-propynyl or cyanomethyl; and $Ar^1$, the bicyclic ring, $R^2$ and $R^3$ have any of the meanings defined hereinbefore;

(f) $R^1$ is methyl, ethyl, allyl or 2-propynyl; and $Ar^1$, the bicyclic ring, $R^2$ and $R^3$ have any of the meanings defined hereinbefore;

(g) $R^2$ and $R^3$ together form a group of the formula —$A^1$—X—$A^2$— which, together with the carbon atom to which $A^1$ and $A^2$ are attached, defines a ring having 4 to 7 ring atoms, wherein $A^1$ and $A^2$, which may be the same or different, each is methylene, ethylene, trimethylene or tetramethylene and X is oxy, thio, sulphinyl or sulphonyl, and which ring may bear a substituent selected from fluoro, hydroxy, methyl, methoxy, ethoxy, methylthio, methylsulphinyl, methylsulphonyl, trifluoromethyl and methylenedioxy; and $Ar^1$, the bicyclic ring and $R^1$ have any of the meanings defined hereinbefore; or (h) $R^2$ and $R^3$ together form a group of the formula —$A^1$—X—$A^2$— which, together with the carbon atom to which $A^1$ and $A^2$ are attached, defines a ring having 5 or 6 ring atoms, wherein $A^1$ is ethylene, $A^2$ is methylene or ethylene and X is oxy, and which ring may bear one or two substituents, which may be the same or different, selected from methyl, ethyl and propyl; and $Ar^1$, the bicyclic ring and $R^1$ have any of the meanings defined hereinbefore;

or a pharmaceutically-acceptable salt thereof.

A preferred compound of the invention comprises a bicyclic derivative of the formula I wherein $Ar^1$ is phenyl or naphth-2-yl which may optionally bear one or two substituents selected from fluoro, chloro, cyano, methyl, ethyl, propyl, tert-butyl, methoxy, methylthio, methylsulphinyl, methylsulphonyl and 2-cyanoprop-2-yl;

the bicyclic ring may optionally bear one substituent selected from fluoro, hydroxy, methoxy and trifluoromethyl;

$R^1$ is methyl, ethyl or allyl; and $R^2$ and $R^3$ together form a group of the formula —$A^1$—X—$A^2$— which, together with the carbon atom to which $A^1$ and $A^2$ are attached, defines a ring having 5 or 6 ring atoms, wherein $A^1$ is ethylene, $A^2$ is methylene or ethylene and X is oxy or thio, and which ring may bear a substituent selected from fluoro, methyl, methoxy and trifluoromethyl;

or a pharmaceutically-acceptable salt thereof.

A further preferred compound of the invention comprises a bicyclic derivative of the formula I wherein $Ar^1$ is phenyl which may optionally bear one or two substituents selected from fluoro, chloro, methyl, ethyl, propyl, tert-butyl, methylthio, methylsulphinyl, methylsulphonyl, trifluoromethyl, phenyl and benzoyl, and wherein said phenyl or benzoyl substituent may optionally bear a substituent selected from fluoro, chloro, methyl and methoxy; or $Ar^1$ is naphth-2-yl which may optionally bear a fluoro substituent;

the bicyclic ring bears no additional substituents;

$R^1$ is methyl, ethyl, allyl or 2-propynyl; and $R^2$ and $R^3$ together form a group of the formula —$A^1$—X—$A^2$— which, together with the carbon atom to which $A^1$ and $A^2$ are attached, defines a ring having 5 or 6 ring atoms, wherein $A^1$ is ethylene, $A^2$ is methylene or ethylene and X is oxy, and which ring may bear one or two substituents, which may be the same or different, selected from methyl, ethyl and propyl;

or a pharmaceutically-acceptable salt thereof.

A further preferred compound of the invention comprises a bicyclic derivative of the formula I wherein $Ar^1$ is phenyl which may optionally bear one or two substituents selected from fluoro, chloro, methyl, ethyl, propyl, tert-butyl, methylthio, methylsulphinyl and 2-cyanoprop-2-yl; or $Ar^1$ is naphth-2-yl which may optionally bear a fluoro substituent; the bicyclic ring may optionally bear one substituent selected from fluoro, methoxy and trifluoromethyl;

$R^1$ is methyl, ethyl or allyl; and $R^2$ and $R^3$ together form a group of the formula —$A^1$—X—$A^2$— which, together with the carbon atom to which $A^1$ and $A^2$ are attached, defines a ring having 5 or 6 ring atoms, wherein $A^1$ is ethylene, $A^2$ is methylene or ethylene and X is oxy, and which ring may bear a substituent selected from methyl and methoxy;

or a pharmaceutically-acceptable salt thereof.

A further preferred compound of the invention comprises a bicyclic derivative of the formula I wherein $Ar^1$ is 4-propylphenyl, 4-methylthiophenyl, 4-methylsulphinylphenyl or naphth-2-yl;

the bicyclic ring bears no additional substituents;

$R^1$ is methyl; and $R^2$ and $R^3$ together form a group of the formula —$A^1$—X—$A^2$— which, together with the carbon atom to which $A^1$ and $A^2$ are attached, defines a ring having 6 ring atoms, wherein each of $A^1$ and $A^2$ is ethylene and X is oxy and which ring may bear a methyl substituent alpha to X;

or a pharmaceutically-acceptable salt thereof.

Specific especially preferred compounds of the invention include, for example, the following bicyclic derivatives of the formula I, or pharmaceutically-acceptable salts thereof:

5-(4-methoxytetrahydropyran-4-yl)-2-(naphth-2-yl)benzo-1,3-dioxole, 5-(4-methoxytetrahydropyran-4-yl)-2-(4-propylphenyl)benzo-1,3-dioxole, 5-(4-methoxytetrahydropyran-4-yl)-2-(4-methylthiophenyl)benzo-1,3-dioxole, 5-(4-methoxytetrahydropyran-4-yl)-2-(4-methylsulphinylphenyl)benzo-1,3-dioxole and 5-[(2RS,4SR)-4-methoxy-2-methyltetrahydropyran-4-yl]-2-(naphth-2-yl)benzo-1,3-dioxole.

A compound of the invention comprising a bicyclic derivative of the formula I as defined hereinbefore, or a pharmaceutically-acceptable salt thereof, may be prepared by any process known to be applicable to the preparation of structurally-related compounds. Such processes are provided as a further feature of the invention. For the purpose of illustration non-limiting examples of the application of such processes are provided hereinafter. Within the description of these processes $Ar^1$, the bicyclic ring, $R^1$, $R^2$ and $R^3$ have any of the meanings defined hereinbefore. Alternatively, where appropriate, conventional protecting groups are utilised on functional groups which would otherwise interfere with the required process. Examples of such conventional protecting groups are provided hereinafter.

Thereafter any protecting group is removed by conventional means.

(a) The alkylation, in the presence of a suitable base, of a compound of the formula II with a compound of the formula $R^1$—Z wherein Z is a displaceable group.

A suitable displaceable group Z is, for example, a halogeno or sulphonyloxy group, for example a chloro, bromo, iodo, methanesulphonyloxy or toluene-p-sulphonyloxy group.

A suitable base for the alkylation reaction is, for example, an alkali or alkaline earth metal carbonate, (1-4C)alkoxide, hydroxide or hydride, for example sodium carbonate, potassium carbonate, sodium ethoxide, sodium butoxide, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

(b) The oxidative rearrangement of a compound of the formula III in the presence of a suitable oxidising agent.

A suitable oxidising agent is, for example, any agent known in the art for such an oxidative rearrangement, for example sodium or potassium metaperiodate. In general the reaction is carried out in a suitable solvent or diluent such as a polar solvent, for example aqueous methanol or aqueous ethanol and at a temperature in the range, for example, 15° to 35° C., conveniently at or near ambient temperature.

(c) The alkylation, in the presence of a suitable base, of a compound of the formula IV with a compound of the formula $Ar^1$—CH(Z)$_2$ wherein Z is a suitable displaceable group as defined hereinbefore.

A suitable base for the alkylation reaction is, for example, one of the bases defined hereinbefore within the disclosure of process variant (a). Alternatively a suitable base is, for example, an organic base such as, for example, triethylamine, N-methylmorpholine, piperidine or pyridine. In general the reaction is carried out in a suitable solvent or diluent such as, for example, an excess of one of the above-mentioned organic bases, or N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near 100° C.

(d) The cyclisation, in the presence of a suitable acid, of a compound of the formula IV with an aldehyde of the formula $Ar^1$—CHO.

A suitable acid for the cyclisation reaction is, for example, an inorganic acid such as hydrochloric, sulphuric or phosphoric acid, for example, an organic acid such as p-toluenesulphonic acid or trifluoroacetic acid. The cyclisation reaction is conveniently performed in a suitable inert solvent or diluent, for example toluene or 1,2-dimethoxyethane. The cyclisation is effected at a temperature in the range, for example, 20° to 150° C., conveniently at or near the boiling point of the diluent or solvent and under conditions wherein the water produced as the cyclisation proceeds is separated, for example by use of a Dean and Stark apparatus.

(e) For the production of those compounds of the formula I wherein $Ar^1$ bears an alkylsulphinyl or alkylsulphonyl substituent; or wherein $R^2$ and $R^3$ together form a group of the formula —$A^1$—X—$A^2$— and X is a sulphinyl or sulphonyl group, and which may bear one or two alkylsulphinyl or alkylsulphonyl groups; the oxidation of a compound of the formula I wherein $Ar^1$ bears an alkylthio substituent; or wherein $R^2$ and $R^3$ together form a group of the formula —$A^1$—X—$A^2$— and X is a thio group, and which may bear one or two alkylthio groups.

A suitable oxidising agent is, for example, any agent known in the art for the oxidation of thio to sulphinyl and/or sulphonyl, for example, hydrogen peroxide, a peracid (such as m-chloroperbenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(f) For the production of those compounds of the formula I wherein $R^1$ is alkanoyl or benzoyl optionally bearing a substituent as defined hereinbefore, the acylation of a compound of the formula I wherein $R^1$ is hydrogen. For the production of those compounds of the formula I wherein $R^1$ is alkanoyl the acylation reaction may be carried out using, for example, a suitable acylating agent.

A suitable acylating agent is, for example, any agent known in the art for the acylation of hydroxy to alkanoyl, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. For the production of those compounds of the formula I wherein $R^1$ is benzoyl optionally bearing a substituent the acylation may be carried out using, for example, a benzoyl halide, for example a benzoyl chloride or bromide, in the presence of a suitable base as defined hereinbefore. In general the reaction is carried out in a suitable solvent or diluent such as methylene chloride, acetone, tetrahydrofuran or tert-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

As stated previously conventional protecting groups are utilised, where appropriate, within the process variants described hereinbefore. Examples of such protecting groups are provided below:

A suitable protecting group for an amino, imino or alkylamino group is, for example, an acyl group for example a (1-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (1-4C)alkanoyl group (especially acetyl), an aroyl group (especially benzoyl) or an arylmethyl group (especially benzyl). The deprotection conditions for the above protecting groups will necessarily vary with the coice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formulae II, III and IV described within process variants a) to (d) above may be obtained by standard procedures of organic chemistry. The preparation of examples of such starting materials is described within the accompanying non-limiting Examples which are provided for the purpose of illustration only. Other necessary starting materials are obtainable by analogous procedures to those described or by modifications thereto which are within the ordinary skill of an organic chemist.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae II, III and IV and these are provided as a further feature of the invention.

As stated previously, the bicyclic derivatives of the formula I are inhibitors of the enzyme 5-LO. The effects of this inhibition may be demonstrated using one or more of the standard procedures set out below:

a) An in-vitro spectrophotometric enzyme assay system, which assesses the inhibitory properties of a test compound in a cell free system using 5-LO isolated from guinea pig neutrophils and as described by D. Aharony and R. L. Stein (J. Biol. Chem., 1986, 261(25), 11512-11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, Brit. J. Pharmacol. 1985, 84, 34P) which involves the use of a protein-$LTB_4$ conjugate produced using the procedure of Young et alia (Prostaglandins, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, Biochem. Pharmacol., 1983, 32, 2319-2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (Brit. J. Pharmacol., 1986, 89, 431-438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (British J. Pharmacology, 1983, 78(1), 67-574). This test provides a further in vivo test for detecting 5-LO inhibitors.

g) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)-f):

Test a): $IC_{50}$ in the range, for example, 0.05-30 $\mu M$;

Test b): $IC_{50}$ ($LTB_4$) in the range, for example, 0.05-40 $\mu M$; $IC_{50}$ ($TxB_2$) in the range, for example, 40-200 $\mu M$;

Test c): oral $ED_{50}$ ($LTB_4$) in the range, for example, 1-100 mg/kg;

Test d): $IC_{50}$ ($LTC_4$) in the range, for example, 0001-1 $\mu M$; $IC_{50}$ ($PGE_2$) in the range, for example, 20-1000 $\mu M$;

Test e): inhibition of inflammation in the range, for exmaple, 0.3-100 $\mu g$ intradermally;

Test f): $ED_{50}$ in the range, for example, 0.5-10 mg/kg i.v:

Test g): oral $ED_{50}$ ($LTB_4$) in the range for example, 0.5-50 mg/kg.

No overt toxicity or other untoward effects are present in tests c), e), f) and/or g) when compounds of the formula I are administered at several multiples of their minimum inhibitory dose or concentration.

Thus, by way of example, the compound 5-(4-methoxytetrahydropyran-4-yl)-2-(naphth-2-yl)benzo-1,3-dioxole has an $IC_{50}$ of 0.3 $\mu M$ against $LTB_4$ in test b), an oral $ED_{50}$ of 5 mg/kg versus $LTB_4$ in test c), and an oral $ED_{50}$ of <3 mg/kg versus $LTB_4$ in test g). In general those compounds of the formula I which are particularly preferred have an $IC_{50}$ of <1 $\mu M$ against $LTB_4$ in test b), and an oral $ED_{50}$ of <100 mg/kg against $LTB_4$ in tests c) and g).

These compounds are examples of bicyclic derivatives of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a bicyclic derivative of the formula I as defined hereinbefore, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a supppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is a bicyclic derivative of the formula I as defined hereinbefore, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a bicyclic derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a bicyclic derivative of the formula I will naturally vary according to the nature and severity of the conditions, the age and sex of the animal or patient and the route of administration, according to well known principles of medicine. As mentioned above, bicyclic derivatives of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a bicyclic derivative of the formula I as defined hereinbefore, or a pharmaceutically-acceptable salt thereof, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°-25° and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture; and (viii) the following abbreviations have been used:
THF: tetrahydrofuran;
DMF: N,N-dimethylformamide;
CH$_2$Cl$_2$: methylene chloride.

EXAMPLE 1

A mixture of 5-(4-hydroxytetrahydropyran-4-yl)-2-(naphth-2-yl)benzo-1,3-dioxole (0.44 g), sodium hydride (50% w/w dispersion in mineral oil; 0.075 g) and THF (8 ml) was stirred at ambient temperature for 40 minutes. Methyl iodide (0.65 ml) was added and the mixture was stirred at ambient temperature for 16 hours. A saturated aqueous ammonium chloride solution (10 ml) was added and the mixture was extracted with ethyl acetate (3×20 ml). The combined organic extracts were dried (MgSO$_4$), decolourised with charcoal and evaporated. There was thus obtained 5-(4-methoxytetrahydropyran-4-yl)-2-(naphth-2-yl)benzo-1,3-dioxole (0.42 g, 92%), m.p. 108°-110° C.

The 5-(4-hydroxytetrahydropyran-4-yl)-2-(naphth-2-yl)benzo-1,3-dioxole used as a starting material was obtained as follows:

A solution of 5-bromosalicylaldehyde (2 g) in diethyl ether (20 ml) was added to (2-naphthyl)magnesium bromide [prepared by adding a solution of 2-bromonaphthalene in diethyl ether (30 ml) to a mixture of magnesium turnings (0.49 g) and diethyl ether (20 ml) and heating the resultant mixture to reflux for 90 minutes] and the mixture was stirred at ambient temperature for 1 hour. A saturated aqueous ammonium chloride solution (20 ml) was added and the mixture was extracted with ethyl acetate (3×20 ml). The combined organic extracts were dried (MgSO$_4$) and evaporated. The residue was purified by column chromatography using increasingly polar mixtures of petroleum ether (b.p. 60°-80° C.) and ethyl acetate as eluent to give 5-bromo-2-hydroxy-α-(2-naphthyl)benzyl alcohol (1.98 g, 60%), m.p. 115°-117° C.

Using a similar procedure to that described in Tet. Let., 1973, 197, a solution of sodium metaperiodate (1.34 g) in water (18 ml) was added to a solution of a portion (1.65 g) of the product so obtained in methanol (94 ml) and the mixture was stirred at ambient temperature for 16 hours. The mixture was filtered and the solid was washed with water. The solid was dried to give 5-bromo-2-(naphth-2-yl)benzodioxole (0.6 g, 37%), m.p. 104°-106° C.

After repetition of the above steps a solution of n-butyllithium (1.5M in hexane; 1.46 ml) was added to a mixture of the product (0.654 g) so obtained and THF (15 ml) which had been cooled to −78° C. The mixture was stirred at −78° C. for 10 minutes and then a solution of tetrahydropyran-4-one (0.23 ml) in THF (2 ml) was added. The mixture was stirred at −78° C. for 30 minutes. The mixture was allowed to warm to −10° C. and a saturated aqueous ammonium chloride solution (20 ml) was added. The mixture was extracted with ethyl acetate (3×20 ml) and the combined extracts were dried (MgSO$_4$) and evaporated. The residue was purified by column chromatography using increasingly polar mixtures of hexane and ethyl acetate as eluent. There was thus obtained the required starting material (0.44 g, 63%) as a white foam.

EXAMPLE 2

Using a similar procedure to that described in Example 1, except that the appropriate 2-substituted benzo-1,3-dioxole was used in place of 5-(4-hydroxytetrahydropyran-4-yl)-2-(naphth-2-yl)benzo-1,3-dioxole and the appropriate alkylating agent was used, there were obtained the compounds described in the following table:

TABLE I

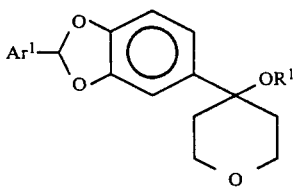

Ex. 2

| Compd. No. | Ar¹ | R¹ | m.p. (°C.) | Yield (%) |
|---|---|---|---|---|
| 1[a] | 4-propylphenyl | Me | oil | 77 |
| 2[b] | 4-propylphenyl | CH₂—C≡CH | oil | 21 |
| 3[c] | 4-methoxy-propyl | Me | 101-102 | 66 |
| 4[d] | 3-trifluoro-methylphenyl | Me | oil | 81 |
| 5[e] | 4-methylthio-phenyl | Me | 70-72 | 82 |
| 6[f] | phenyl | Me | oil | 82 |
| 7[g] | naphth-2-yl | CH₂—CH=CH₂ | oil | 95 |

Notes

[a]The product was purified by column chromatography using increasingly polar mixtures of hexane and ethyl acetate as eluent and it gave the following NMR data:-
(CD₃SOCD₃, δ values) 0.9 (t, 3H), 1.6 (m, 2H), 1.83–1.95 (m, 4H), 2.6 (t, 2H), 2.88 (s, 3H), 3.62–3.72 (m, 4H), 6.84–6.94 (m, 2H), 6.95 (d, 1H), 7.1 (s, 1H), 7.3 (d, 2H), 7.47 (d, 2H).
The 5-(4-hydroxytetrahydropyran-4-yl)-2-(4-propylphenyl)benzo-1,3-dioxole used as a starting material was obtained using a similar procedure to that described in the portion of Example 1 which is concerned with the preparation of starting materials except that 4-propylphenylmagnesium bromide was used as the Grignard reagent. There was thus obtained the required starting material as an oil in 37% yield.

[b]The starting material required immediately above was alkylated with 2-propynyl bromide using the following procedure:-
2-Propynyl bromide (80% w/v solution in toluene, 0.15 ml) was added dropwise to a mixture of the required starting material (0.34 g), powdered potassium hydroxide (0.1 g), 1,4,7,10,13,16-hexaoxacyclooctadecane (hereinafter 18-crown-6, 0.011 g) and THF (2.5 ml) and the mixture was stirred at ambient temperature for 18 hours. Second portions of each of potassium hydroxide (0.1 g), 18-crown-6 (0.02 g) and 2-propynyl bromide (80% w/v solution, 0.15 ml) were added and the mixture was stirred for a further 20 hours. The mixture was partitioned between ethyl acetate and a saturated aqueous ammonium chloride solution. The organic solution was washed with water and with brine, dried (MgSO₄) and evaporated. The residue was purified by column chromatography using increasingly polar mixtures of hexane and ethyl acetate as eluent. There was thus obtained 2-(4-propyl-phenyl)-5-(4-(prop-2-ynyloxy)tetrahydropyran-4-yl)benzo-1,3-dioxole (0.08 g, 21%) as an oil.
NMR Spectrum (CD₃SOCD₃, δ values) 0.9 (t, 3H), 1.6 (m, 2H), 1.84–1.98 (m, 4H), 2.6 (t, 2H), 3.3 (t, 1H), 3.26–3.78 (m, 6H), 6.9 (m, 2H), 6.97 (d, 1H), 7.13 (s, 1H), 7.3 (d, 2H), 7.47 (d, 2H).

[c]The product was purified by column chromatography using increasingly polar mixtures of hexane and ethyl acetate as eluent. The 5-(4-hydroxytetrahydropyran-4-yl)-2-(4-methoxyphenyl)benzo-1,3-dioxane used as a starting material was obtained as follows:-
A mixture of 4-methoxybenzaldehyde (2.04 g), 4-bromocatechol (2.84 g), p-toluenesulphonic acid (2 mg) and toluene (12.5 ml) was heated to reflux for 6 hours utilizing a Dean and Stark water separating condenser. The product was purified by column chromatography, the reaction mixture being poured onto a column of silica and increasingly polar mixtures of hexane and toluene being used as eluent. There was thus obtained 5-bromo-2-(4-methoxyphenyl)benzo-1,3-dioxole (1.1 g, 24%), m.p. 45-46° C.
Using a similar procedure to that described in the 3rd paragraph of the portion of Example 1 which is concerned with the preparation of starting materials the product obtained immediately above was reacted with tetrahydropyran-4-one to give the required starting material in 44% yield, as an oil.

[d]The product was purified by column chromatography using increasingly polar mixtures of hexane and ethyl acetate as eluent and it gave the following NMR data:-
(CD₃SOCD₃, δ values) 1.87–1.94 (m, 4H), 2.98 (s, 3H), 3.63–3.72 (m, 4H), 6.9 (doublet of doublets, 1H), 6.97 (d, 1H), 7.0 (d, 1H), 7.29 (s, 1H), 7.7–7.93 (m, 4H).

The 5-(4-hydroxytetrahydropyran-4-yl)-2-(3-trifluoromethyl-phenyl)benzo-1,3-dioxole used as a starting material was obtained using a similar procedure to that described in Note c. immediately above except that 3-trifluoromethylbenzaldehyde was used in place of 4-methoxybenzaldehyde. There was thus obtained the required starting material as an oil, in 6% yield.

[e]The product was purified by column chromatography using increasingly polar mixtures of hexane and ethyl acetate as eluent. The 5-(4-hydroxytetrahydropyran-4-yl)-2-(4-methylthio-phenyl)benzo-1,3-dioxole used as a starting material was obtained using a similar procedure to that described in Note c. above except that 4-methylthiobenzaldehyde was used in place of 4-methoxybenzaldehyde. There was thus obtained the required starting material in 12% yield, m.p. 108–110° C.

[f]The product was purified by column chromatography using increasingly polar mixtures of hexane and ethyl acetate as eluent and it gave the following NMR data:-
(CD₃SOCD₃, δ values) 1.82–1.94 (m, 4H), 2.88 (s, 3H), 3.64–3.74 (m, 4H), 6.85–6.96 (m, 2H), 6.98 (d, 1H), 7.16 (s, 1H), 7.45–7.6 (m, 5H).
The 5-(4-hydroxytetrahydropyran-4-yl)-2-phenylbenzo-1,3-dioxole used as a starting material was obtained as follows:-
A mixture of benzylidene chloride (1.61 g), 4-bromocatechol (1.89 g) and pyridine (15 ml) was heated to reflux for 18 hours. The mixture was evaporated and the residue was partitioned between CH₂Cl₂ and water. The organic phase was washed with a 0.5N sodium hydroxide solution, with water and with brine, dried (MgSO₄) and evaporated. The residue was purified by column chromatography using hexane as eluent to give 5-bromo-2-phenylbenzo-1,2-dioxole (1.13 g, 41%) as a liquid.
NMR Spectrum (CD₃SOCD₃, δ values) 6.93 (d, 1H), 7.05 (doublet of doublets, 1H), 7.2 (d, 1H), 7.23 (s, 1H), 7.45–7.6 (m, 5H).
Using a similar procedure to that described in the 3rd paragraph of the portion of Example 1 which is concerned with the preparation of starting materials the product obtained immediately above was reacted with tetrahydropyran-4-one to give the required starting material in 78% yield, m.p. 128-129° C.

[g]The product was purified by column chromatography using increasingly polar mixtures of hexane and ethyl acetate as eluent and it gave the following NMR data:-
(CD₃SOCD₃, δ values) 1.85–2.0 (m, 4H), 3.57 (m, 2H), 3.65–3.76 (m, 4H), 5.08 (m, 1H), 5.27 (m, 1H), 5.78–5.96 (m, 1H), 6.96 (m, 2H), 7.04 (d, 1H), 7.34 (s, 1H), 7.56–7.68 (m, 3H), 7.95–8.06 (m, 3H), 8.17 (d, 1H).

EXAMPLE 3

A mixture of 5-[(2RS,4SR)-4-hydroxy-2-methyltetrahydropyran-4-yl]-2-(naphth-2-yl)benzo-1,3-dioxole (0.33 g), sodium hydride (50% w/w dispersion in mineral oil, 0.06 g) and DMF (3 ml) was stirred at ambient temperature for 30 minutes. Methyl iodide (0.2 ml) was added and the mixture was stirred at ambient temperature for 18 hours. A saturated aqueous ammonium chloride solution (10 ml) was added and the mixture was extracted with ethyl acetate (3×10 ml). The combined organic extracts were dried (MgSO₄) and evaporated. The residue was purified by column chromatography using increasingly polar mixtures of hexane and ethyl acetate as eluent. There was thus obtained 5-[(2RS,4SR)-4-methoxy-2-methyltetrahydropyran-4-yl]-2-(naphth-2-yl)benzo-1,3-dioxole (0.18 g, 53%) as an oil.

NMR Spectrum (CD₃SOCD₃, δ values) 1.10 (d, 3H), 1.35–1.53 (m, 1H), 1.7–2.06 (m, 3H), 2.89 (s, 3H), 3.64–3.82 (m, 3H), 6.90 (doublet of doublets, 1H), 6.96 (d, 1H), 7.0 (d, 1H), 7.32 (s, 1H), 7.54–7.7 (m, 3H), 7.94–8.06 (m, 3H), 8.16 (d, 1H).

The 5-[(2RS,4SR)-4-hydroxy-2-methyltetrahydropyran-4-yl]-2-(naphth-2-yl)benzo-1,3-dioxole used as a starting material was obtained as follows:

A solution of n-butyl-lithium (1.4M in hexane, 2.35 ml) was added to a solution of 5-bromo-2-(naphth-2-yl)benzo-1,3-dioxole (0.98 g) in THF (22 ml) which had been cooled to −78° C. and the mixture was stirred at this temperature for 5 minutes. A solution of magnesium bromide etherate (0.95 g) in a mixture of toluene and diethyl ether was added and the reaction mixture was stirred at −78° C. for 15 minutes. A solution of 2-methyltetrahydropyran-4-one (0.36 g) in THF (3 ml) was added and the mixture was stirred at −78° C. for 30 minutes and then at ambient temperature for 3 hours. A saturated aqueous ammonium chloride solution (20 ml) was added and the mixture was extracted with ethyl acetate (3×20 ml). The combined organic extracts were washed with water and with brine, dried (MgSO₄) and evaporated. The residue was purified by column chromatography using increasingly polar mixtures of hexane and ethyl acetate as eluent. There were thus obtained and separated the following diastereoisomers:

a less polar diastereoisomer:

5-[(2RS,4SR)-4-hydroxy-2-methyltetrahydropyran-4-yl]-2-(naphth-2-yl)benzo-1,3-dioxole (0.24 g, 22%), as an oil, wherein the 2-methyl and 4-hydroxy substituents around the tetrahydropyran ring are in a trans relationship; and a more polar diastereoisomer:

5-[(2SR,4SR)-4-hydroxy-2-methyltetrahydropyran-4-yl]-2-(naphth-2-yl)benzo-1,3-dioxole (0.24 g, 22%), as an oil, wherein the 2-methyl and 4-hydroxy substituents around the tetrahydropyran ring are in a cis relationship.

EXAMPLE 4

The procedure described in Example 3 was repeated except that the more polar diastereoisomer described in the portion of Example 3 which is concerned with the preparation of starting materials was used as a starting material. There was thus obtained 5-[(2SR,4SR)-4-methoxy-2-methyltetrahydropyran-4-yl]-2-(naphth-2-yl)benzo-1,3-dioxole as an oil in 63% yield.

NMR Spectrum (CD₃SOCD₃, δ values) 1.17 (d, 3H), 1.49 (doublet of doublets, 1H), 1.66-1.86 (m, 1H), 2.33-2.55 (m, 2H), 2.85 (s, 3H), 3.26-3.46 (m, 2H), 3.9 (m, 1H), 6.96-7.09 (m, 2H), 7.12 (s, 1H), 7.36 (s, 1H), 7.6-7.73 (m, 3H), 7.99-8.08 (m, 3H), 8.2 (d, 1H).

EXAMPLE 5

A solution of sodium metaperiodate (0.25 g) in water (2 ml) was added to a mixture of 5-(4-methoxytetrahydropyran-4-yl)-2-(4-methylthiophenyl)benzo-1,3-dioxole (0.4 g; Example 2, Compound No. 5), methanol (20 ml) and water (2 ml) and the mixture was stirred at ambient temperature for 18 hours. The mixture was partitioned between ethyl acetate and water. The organic phase was separated, dried (MgSO₄) and evaporated. The residue was purified by column chromatography using increasingly polar mixtures of ethyl acetate and acetone as eluent. There was thus obtained 5-(4-methoxytetrahydropyran-4-yl)-2-(4-methylsulphinylphenyl)benzo-1,3-dioxole (0.31 g, 74%) as an oil.

NMR Spectrum (CD₃SOCD₃, δ values) 1.8-1.95 (m, 4H), 2.76 (s, 3H), 2.87 (s, 3H), 3.6-3.73 (m, 4H), 6.8 (doublet of doublets, 1H), 6.95 (d, 1H), 6.98 (d, 1H), 7.25 (s, 1H), 7.77 (s, 4H).

EXAMPLE 6

A mixture of 5-(4-methoxytetrahydropyran-4-yl)-2-(4-methylthiophenyl)benzo-1,3-dioxole (0.35 g), m-chloroperbenzoic acid (0.6 g) and ethyl acetate (70 ml) was stirred at ambient temperature for 18 hours. The mixture was washed with a saturated aqueous potassium carbonate solution and with brine. The organic solution was ried (MgSO₄) and evaporated. The residue was purified by column chromatography using increasingly polar mixture of hexane and ethyl acetate as eluent. There was thus obtained 5-(4-methoxytetrahydropyran-4-yl)-2-(4-methylsulphonylphenyl)benzo-1,3-dioxole (0.33 g, 86%), m.p. 52° C.

CHEMICAL FORMULAE

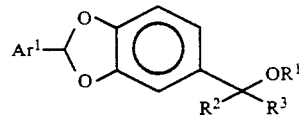

I

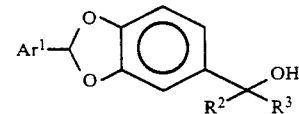

II

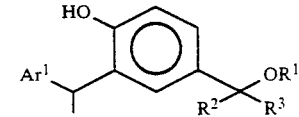

III

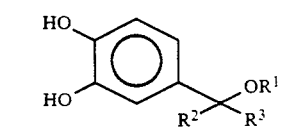

IV

What we claim is:

1. A bicyclic derivative of the formula I

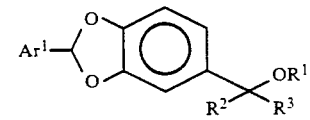

I wherein $Ar^1$ is phenyl or naphthyl which may optionally bear one or more substituents selected from amino, halogeno, hydroxy, cyano, (1–4C)alkyl, (2–4C)alkenyl, (2–4C)alkynyl, (1–4C)alkoxy, (1–4C)alkylthio, (1–4C)alkylsulphinyl, (1–4C)alkylsulphonyl, (1–4C)alkylamino, di-[(1–4C)alkyl]amino, (1–4C)alkoxycarbonyl, (2–4C)alkanoyl, hydroxy-(1–4C)alkyl, fluoro-(1–4C)alkyl, cyano-(1–4C)alkyl, fluoro-(1–4C)alkoxy, cyano-(1–4C)alkoxy, phenyl and benzoyl, and wherein said phenyl or benzoyl substituent may optionally bear a substituent selected from halogeno, (1–4C)alkyl and (1–4C)alkoxy;

wherein the bicyclic ring may optionally bear one or two substituents selected from halogeno, hydroxy, (1–4C)alkyl, (1–4C)alkoxy and fluoro-(1–4C)alkyl;

wherein $R^1$ is (1–6C)alkyl, (3–6C)alkenyl, (3–6C)alkynyl, cyano-(1–4C)alkyl or (2–4C)alkanoyl or $R^1$ is benzoyl which may optionally bear a substituent selected from halogeno, (1–4C)alkyl and (1–4C)alkoxy; and wherein $R^2$ and $R^3$ together form a group of the formula —$A^1$—X—$A^2$— which, together with the carbon atom to which $A^1$ and $A^2$ are attached, defines a ring having 6 ring atoms, wherein $A^1$ and $A^2$, which may be the same or different, each is (1–4C)alkylene and X is oxy, and which ring may bear one or two substituents, which may be the same or different, selected from halogeno, hydroxy, (1-4C)alkyl, (1-4C)alkoxy, (1-4C)alkylthio, (1-4C)alkylsulphinyl and (1-4C)alkylsulphonyl;

or a pharmaceutically-acceptable salt thereof.

2. A bicyclic derivative of the formula I as claimed in claim 1 wherein
- $Ar^1$ is phenyl or naphth-2-yl which may optionally bear one or two substituents selected from fluoro, chloro, cyano, methyl, ethyl, propyl, tert-butyl, methoxy, methylthio, methylsulphinyl, methylsulphonyl and 2-cyanoprop-2-yl;
- the bicyclic ring may optionally bear one substituent selected from fluoro, hydroxy, methoxy and trifluoromethyl;
- $R^1$ is methyl, ethyl or allyl; and
- $R^2$ and $R^3$ together form a group of the formula $-A^1-X-A^2-$ which, together with the carbon atom to which $A^1$ and $A^2$ are attached, defines a ring having 6 ring atoms, wherein $A^1$ is ethylene, $A^2$ is methylene or ethylene and X is oxy, and which ring may bear a substituent selected from fluoro, methyl, methoxy and trifluoromethyl;

or a pharmaceutically-acceptable salt thereof.

3. A bicyclic derivative of the formula I as claimed in claim 1 wherein
- $Ar^1$ is phenyl which may optionally bear one or two substituents selected from fluoro, chloro, methyl, ethyl, propyl, tert-butyl, methylthio, methylsulphinyl, methylsulphonyl, trifluoromethyl, phenyl and benzoyl, and wherein said phenyl or benzoyl substituent may optionally bear a substituent selected from fluoro, chloro, methyl and methoxy; or $Ar^1$ is naphth-2-yl which may optionally bear a fluoro substituent;
- the bicyclic ring bears no additional substituents;
- $R^1$ is methyl, ethyl, allyl or 2-propynyl; and
- $R^2$ and $R^3$ together form a group of the formula $-A^1-X-A^2$ which, together with the carbon atom to which $A^1$ and $A^2$ are attached, defines a ring having 6 ring atoms, wherein $A^1$ is ethylene, $A^2$ is methylene or ethylene and X is oxy, and which ring may bear one or two substituents, which may be the same or different, selected from methyl, ethyl and propyl;

or a pharmaceutically-acceptable salt thereof.

4. A bicyclic derivative of the formula I as claimed in claim 1 wherein
- $Ar^1$ is phenyl which may optionally bear one or two substituents selected from fluoro, chloro, methyl, ethyl, propyl, tert-butyl, methylthio, methylsulphinyl and 2-cyanoprop-2-yl; or
- $Ar^1$ is naphth-2-yl which may optionally bear a fluoro substituent;
- the bicyclic ring may optionally bear one substituent selected from fluoro, methoxy and trifluoromethyl;
- $R^1$ is methyl, ethyl or allyl; and
- $R^2$ and $R^3$ together form a group of the formula $-A^1-X-A^2-$ which, together with the carbon atom to which $A^1$ and $A^2$ are attached, defines a ring having 6 ring atoms, wherein $A^1$ is ethylene, $A^2$ is methylene or ethylene and X is oxy, and which ring may bear a substituent selected from methyl and methoxy;

or a pharmaceutically-acceptable salt thereof.

5. A bicyclic derivative of the formula I as claimed in claim 1 wherein
- $Ar^1$ is 4-propylphenyl, 4-methylthiophenyl, 4-methylsulphinylphenyl or naphth-2-yl;
- the bicyclic ring bears no additional substituents;
- $R^1$ is methyl; and
- $R^2$ and $R^3$ together form a group of the formula $-A^1-X-A^2-$ which, together with the carbon atom to which $A^1$ and $A^2$ are attached, defines a ring having 6 ring atoms, wherein each of $A^1$ and $A^2$ is ethylene and X is oxy and which ring may bear a methyl substituent alpha to X;

or a pharmaceutically-acceptable salt thereof.

6. A bicyclic derivative of the formula I as claimed in claim 1, or a pharmaceutically-acceptable salt thereof, selected from the group consisting of:
5-(4-methoxytetrahydropyran-4-yl)-2-(naphth-2-yl)benzo-1,3-dioxole,
5-(4-methoxytetrahydropyran-4-yl)-2-(4-propylphenyl)benzo-1,3-dioxole,
5-(4-methoxytetrahydropyran-4-yl)-2-(4-methylthiophenyl)benzo-1,3-dioxole,
5-(4-methoxytetrahydropyran-4-yl)-2-(4-methylsulphinylphenyl)benzo-1,3-dioxole and
5-[(2RS,4SR)-4-methoxy-2-methyltetrahydropyran-4-yl]-2-(naphth-2-yl)benzo-1,3-dioxole.

7. A pharmaceutical composition which comprises a bicyclic derivative of the formula I, or a pharmaceutically-acceptable salt thereof, as claimed in any one of claims 1 to 6 in association with a pharmaceutically-acceptable diluent or carrier.

8. A method of treating a disease or medical condition mediated alone or in part by one or more leukotrienes which comprises administering to a warm-blooded animal requiring such treatment an effective amount of a bicyclic derivative of the formula I, or a pharmaceutically-acceptable salt thereof, as claimed in any one of claims 1 to 6.

* * * * *